US00PP36819P3

(12) United States Plant Patent
Olesen

(10) Patent No.: US PP36,819 P3
(45) Date of Patent: Jul. 15, 2025

(54) ROSE PLANT NAMED 'Poulvic001'

(50) Latin Name: *Rosa hybrida*
Varietal Denomination: Poulvic001

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 18/831,184

(22) Filed: Sep. 5, 2024

(65) Prior Publication Data

US 2025/0107466 P1 Mar. 27, 2025

(30) Foreign Application Priority Data

Sep. 22, 2023 (QZ) ..... PBR 20231983

(51) Int. Cl.
*A01H 5/02* (2018.01)
*A01H 6/74* (2018.01)

(52) U.S. Cl.
USPC ..... Plt./122
CPC ..... *A01H 6/749* (2018.05)

(58) Field of Classification Search
USPC ..... Plt./122
CPC ..... A01H 6/749; A01H 5/02
See application file for complete search history.

*Primary Examiner* — Keith O. Robinson

(57) ABSTRACT

A new garden rose plant of the Miniature class which has abundant, red flowers and attractive foliage. This new and distinct variety has shown to be uniform and stable in the resulting generations from asexual propagation.

2 Drawing Sheets

Botanical designation: *Rosa hybrida.*

Variety denomination: 'Poulvic001'.

This application claims priority to Plant Breeder's Rights Application Number 2023/1983, which was filed at the Community Plant Variety Rights Office in the European Union on Sep. 22, 2023, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2014 and the resulting seeds were planted in a controlled environment in Fredensborg, Denmark. The new variety, named 'Poulvic001', originated as a single seedling from the stated cross.

The new variety may be distinguished from its male pollen parent and female seed parent primarily by the following characteristics. The male pollen parent plant has red flowers with about 30 flower petals while the new variety has red flowers with 145 petals. The female seed parent plant has red flowers with a diameter of 35 mm while the new variety has red flowers with a diameter of 70 mm.

The objective of the hybridization of this rose variety was to create a new and distinct variety with unique qualities, such as:

1. Uniform and abundant red flowers;
2. Vigorous, but compact growth when propagated on its own roots;
3. Exceptional disease resistance.

This combination of qualities is not present in previously available commercial cultivars of this type, known to the inventor, and distinguish 'Poulvic001' from all other varieties of which we are aware.

As part of the rose development program, Mogens N. Olesen germinated the seeds from the aforementioned hybridization during winter of 2014 and conducted evaluations on the resulting seedlings in a controlled environment in Fredensborg, Denmark. 'Poulvic001' was selected in the spring of 2015 by the inventor as a single plant from the progeny of the aforementioned hybridization.

Asexual reproduction of 'Poulvic001' by rooted cuttings was first done by Mogens N. Olesen in the nursery in Fredensborg, Denmark in July 2015. This initial and other subsequent asexual propagations conducted in controlled environments have demonstrated that the characteristics of 'Poulvic001' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulvic001'.

Specifically illustrated in FIG. 1 of the drawings are fully opened flowers viewed from above and the side, flower petals detached revealing reproductive flower parts, sepals detached showing the flower receptacle.

Figure 1:
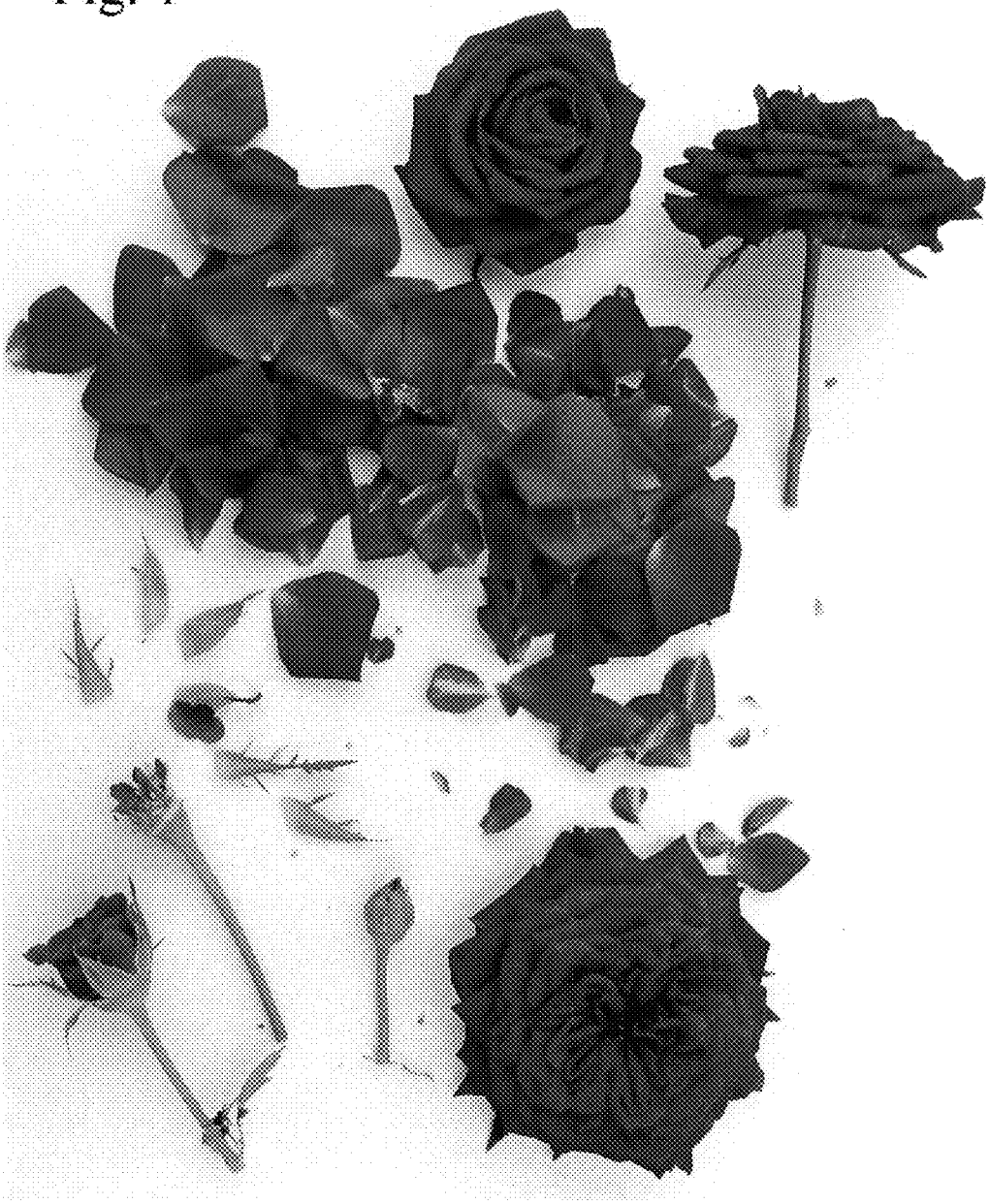
Figure 2:
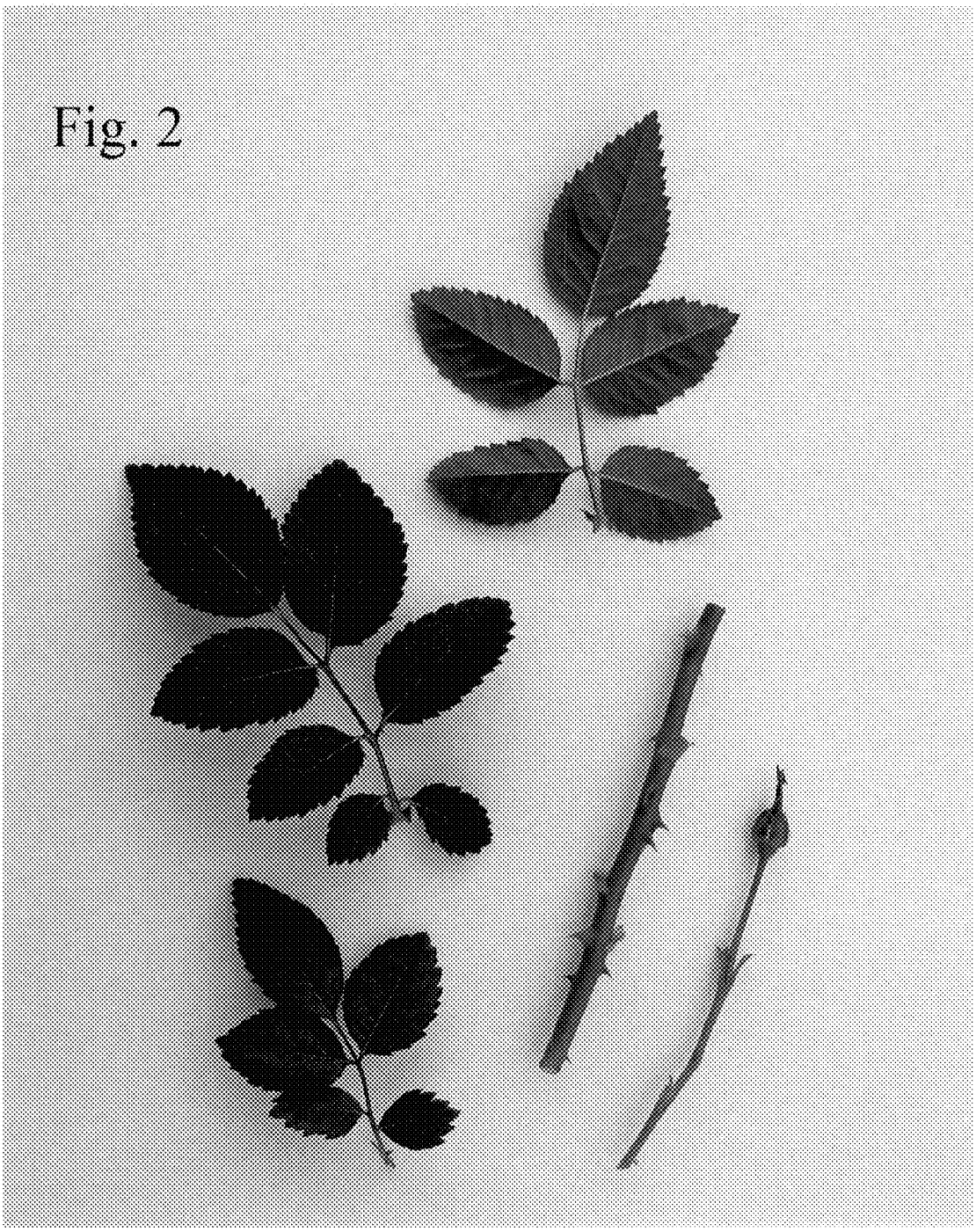

Specifically illustrated in FIG. 2 of the drawings are juvenile and mature leaves, bare stem, and flower bud on the branch. Plants shown are 5 months old.

DETAILED DESCRIPTION OF THE VARIETY

The following is a description of 'Poulvic001', as observed in its growth in a glass house nursery located in Odense Denmark. Observed plants are 5 months of age, and were grown on their own roots in 24 cm containers. Color references are made using The Royal Horticultural Society (London, England) Colour Chart, 2001, except where common terms of color are used.

For a comparison, several physical characteristics of the rose variety 'Poulvic008', U.S. Plant Pat. No. 35,311 are compared to 'Poulvic001' in Chart 1.

CHART 1

| | 'Poulvic001' | 'Poulvic008' |
|---|---|---|
| Petal Count | 145 | 25 |
| Flower Diameter | 70 mm | 75 mm |
| General Tonality of Flower Color | Red Group 45B | Red Group 53C |

FLOWER AND FLOWER BUD

Blooming habit: Continuous.

Flower bud:

*Size*.—Upon opening, 19 mm in length from base of receptacle to end of bud. Bud diameter is 12 mm.

*Bud form*.—Globose.

*Bud color*.—As sepals divide petals are Red Group 53C.

*Sepal inner surface*.—Color: Yellow-Green Group 146D. Surface: Lightly pubescent.

*Sepal outer surface*.—Color: Yellow-Green Group 144A. Texture: Smooth.

*Sepal shape*.—Apex: Cirrhose. Base: Flat at union with receptacle.

*Sepal margin*.—Margins have moderate to strong foliaceous appendages on three of the five sepals.

*Sepal size*.—28 mm long, 9 mm wide.

*Receptacle*.—Texture: Smooth. Size: 10 mm in height, 11 mm wide. Color: Yellow-Green Group 144A. Shape: Funnel.

*Pedicel*.—Surface: Smooth. Length: About 45 mm. Diameter: 3 mm on average. Color: Yellow-Green Group 144A. Strength: Strong.

Flower bud development: Flower buds are borne single.

Flower bloom:

*Fragrance*.—Light floral scent.

*Duration*.—The blooms have a duration on the plant of approximately 21 days. Petals fall cleanly away from plant after flowers have fully matured.

*Size*.—Flower diameter is 70 mm when open. Flower depth is 30 mm.

*Flower shape*.—Quartered-rosette, very double, with many overlapping petals packed into quarter sections.

*Shape of flower, side view*.—The upper portion is convex. The lower portion is concave.

Petalage: Under normal conditions, flowers have about 145 petals.

General tonality of flower: Open flowers are Red Group 45B. After flowers have fully matured general tonality fades to Red-Purple Group N57A and Red Group 45B.

Petal color:

*Upon opening, outer petals*.—Upper surface: Red Group 53B. Lower surface: Red Group 53C.

*Upon opening, inner petals*.—Upper surface: Red Group 53B. Lower surface: Red Group 53C.

*Basal petal spots, upon opening*.—Upper surface: White Group 155C. Lower surface: White Group 155C.

*After opening, outer petals*.—Upper surface: Red Group 53B, with occasional streaks of White Group N155B. Lower surface: Red-Purple Group 58B, with occasional streaks of White Group N155B.

*After opening, inner petals*.—Upper surface: Red Group 53B. Lower surface: Red Group 53C.

*Basal petal spots, after opening*.—Upper surface: White Group 155C. Lower surface: White Group 155C.

Petals:

*Petal reflex*.—Outer petals have strong reflex.

*Margin*.—Entire and uniform. Moderate undulations.

*Shape*.—Broad and elliptic. Apex shape: Rounded. Base shape: Acute.

*Size*.—About 30 to 35 mm (l)×42 mm (w).

*Texture*.—Smooth.

*Thickness*.—Average.

Petaloids:

*Size*.—14 mm (l) by 10 mm (w).

*Quantity*.—About 25.

*Shape*.—Elliptical with an acute base and rounded apices.

*Color*.—Upper Red Group 53B, with occasional streaks of White Group N155B. Lower Red-Purple Group 58B, with occasional streaks of White Group N155B. Upper and lower surface have additional streaking of Red-Purple Group 58D.

Reproductive flower parts:

*Pollen*.—None observed.

*Anthers*.—Size: 1.5 mm in length. Color: Greyed-Orange Group 166A Quantity: 30 on average.

*Filaments*.—Color: White Group 155B. Length: 3 mm.

*Pistils*.—Length: 9 mm. Quantity: 25 on average.

*Stigmas*.—Color: Greyed-Yellow Group 160A.

*Styles*.—Color: White Group 155A with other intonations of Red-Purple Group 58C.

*Location of stigmas*.—Superior in location relative to the length of the filaments and the height of the anthers.

*Hips*.—None Observed.

PLANT

Plant growth: Miniature with upright habit. Plants are 35 cm in height, and 40 cm wide.

Stems:

*Color of juvenile growth*.—Yellow-Green Group 144A.

*Color of mature growth*.—Yellow-Green Group 146B.

*Length*.—Canes are about 25 cm from the base of the plant to the flowering portion.

*Diameter*.—About 5 mm.

*Internodes*.—On mature canes about 32 mm between nodes.

*Surface texture*.—Young wood: Smooth. Older wood: Smooth.

Long prickles:

*Incidence*.—9 prickles per 10 cm of stem.

*Size*.—Average length of prickles on mature stems is 5 mm.

*Shape*.—Upper portion is linear. Lower portion is concave.

*Color*.—Juvenile prickles: Greyed-Red Group 180C. Mature prickles: Greyed-Yellow Group 160B.

Plant foliage:

*Compound leaf*.—110 mm (l)×75 mm (w).

*Quantity*.—About 3 leaves per 10 cm of stem.

*Leaf bearing angle to the stem*.—45 degrees.

*Color of juvenile foliage*.—Upper side: Yellow-Green Group 144A with intonations of Greyed-Orange Group 177A at margins. Lower side: Yellow-Green Group 146C shaded with intonations of Greyed-Orange Group 177A.

*Color of mature foliage*.—Upper side: Yellow-Green Group 147A. Lower side: Yellow-Green Group 148C.

Plant leaves and leaflets:

*Stipules*.—Size: 11 mm long, 3 mm wide. Quantity: 2 per compound leaf. Shape: Linear, slightly broad based with outward extending apices. Margins: Finely serrated. Color: Yellow-Green Group 144A.

*Petiole*.—Length: 20 mm. Diameter: 1.5 mm. Upper surface color: Yellow-Green Group 144A with intonations of Greyed-Purple Group 183A. Lower surface color: Yellow-Green Group 144B.

*Rachis*.—Length: 40 mm. Upper surface color: Yellow-Green Group 146A Lower surface color: Yellow-Green Group 144A.

*Leaflet*.—Quantity: 7 and 5 leaflets. Margins: Serrated. Size: Terminal leaflets are about 56 mm long, 36 mm wide. Shape: Generally elliptical. Base: Rounded. Apex: Acute. Texture: Smooth. Thickness: Average. Arrangement: Odd pinnate. Venation: Reticulate. Glossiness: Not glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulvic001' substantially as described and illustrated herein.

* * * * *